(12) United States Patent
Sachdeva et al.

(10) Patent No.: US 6,250,918 B1
(45) Date of Patent: Jun. 26, 2001

(54) METHOD AND APPARATUS FOR SIMULATING TOOTH MOVEMENT FOR AN ORTHODONTIC PATIENT

(75) Inventors: Rohit Sachdeva, Plano, TX (US); Rudger Rubbert, Berlin (DE)

(73) Assignee: OraMetrix, Inc., Dallas, TX (US)

( * ) Notice: Subject to any disclaimer, the term of this patent is extended or adjusted under 35 U.S.C. 154(b) by 0 days.

(21) Appl. No.: 09/451,609

(22) Filed: Nov. 30, 1999

(51) Int. Cl.⁷ .................................................. A61C 3/00
(52) U.S. Cl. ............................................................. 433/24
(58) Field of Search .............................. 433/24, 215, 72

(56) References Cited

U.S. PATENT DOCUMENTS

| | | | |
|---|---|---|---|
| Re. 35,169 | | 3/1996 | Lemchen et al. .................. 433/24 |
| 5,011,405 | | 4/1991 | Lemchen ............................ 433/24 |
| 5,395,238 | | 3/1995 | Andreiko et al. .................. 433/24 |
| 5,431,562 | * | 7/1995 | Andreiko et al. .................. 433/24 |
| 5,447,432 | * | 9/1995 | Andreiko et al. .................. 433/24 |
| 5,518,397 | | 5/1996 | Andreiko et al. .................. 433/24 |
| 5,533,895 | * | 7/1996 | Andreiko et al. .................. 433/24 |
| 5,618,716 | | 4/1997 | Andreiko et al. .................. 433/11 |
| 5,683,243 | * | 11/1997 | Andreiko et al. ................ 433/24 X |
| 5,879,158 | * | 3/1999 | Doyle et al. ...................... 433/24 |

FOREIGN PATENT DOCUMENTS

EP 0250 993   6/1987   (DE).

* cited by examiner

Primary Examiner—Nicholas D. Lucchesi
(74) Attorney, Agent, or Firm—McDonnell Boehnen Hulbert & Berghoff

(57) ABSTRACT

A method and apparatus for simulating tooth movement for an orthodontic patient include processing that begins by determining, on a tooth by tooth basis, a three-dimensional direct path of movement from a three-dimensional digital model of an actual orthodontic structure and a three-dimensional digital model of a desired orthodontic structure. The processing continues by simulating tooth movement for a plurality of teeth based on each tooth's corresponding three-dimensional direct path. The process then determines whether a conflict arises between at least two teeth of the plurality of teeth, or for a single tooth, during the simulating. If a conflict arose between at least two teeth, the conflict is resolved with respect to a priority tooth of the teeth in conflict.

20 Claims, 4 Drawing Sheets

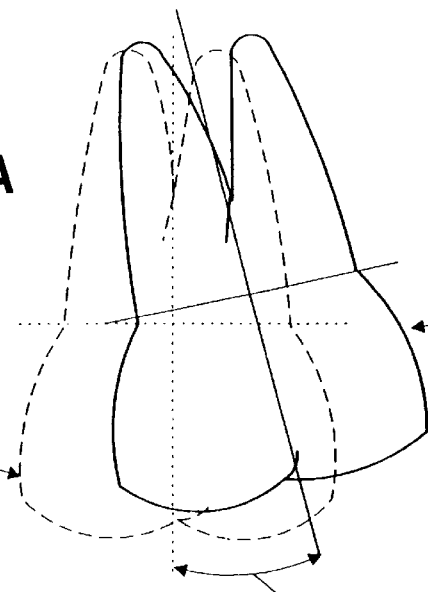
FIG. 3A
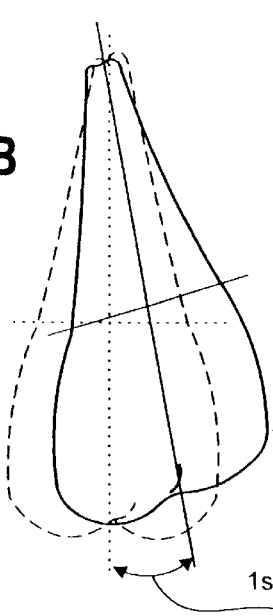
FIG. 3B
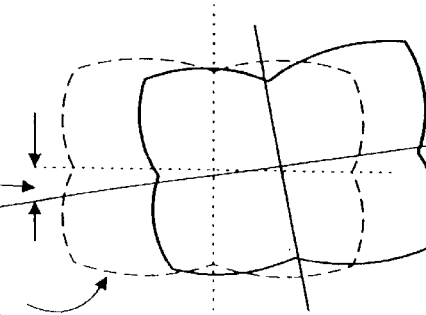

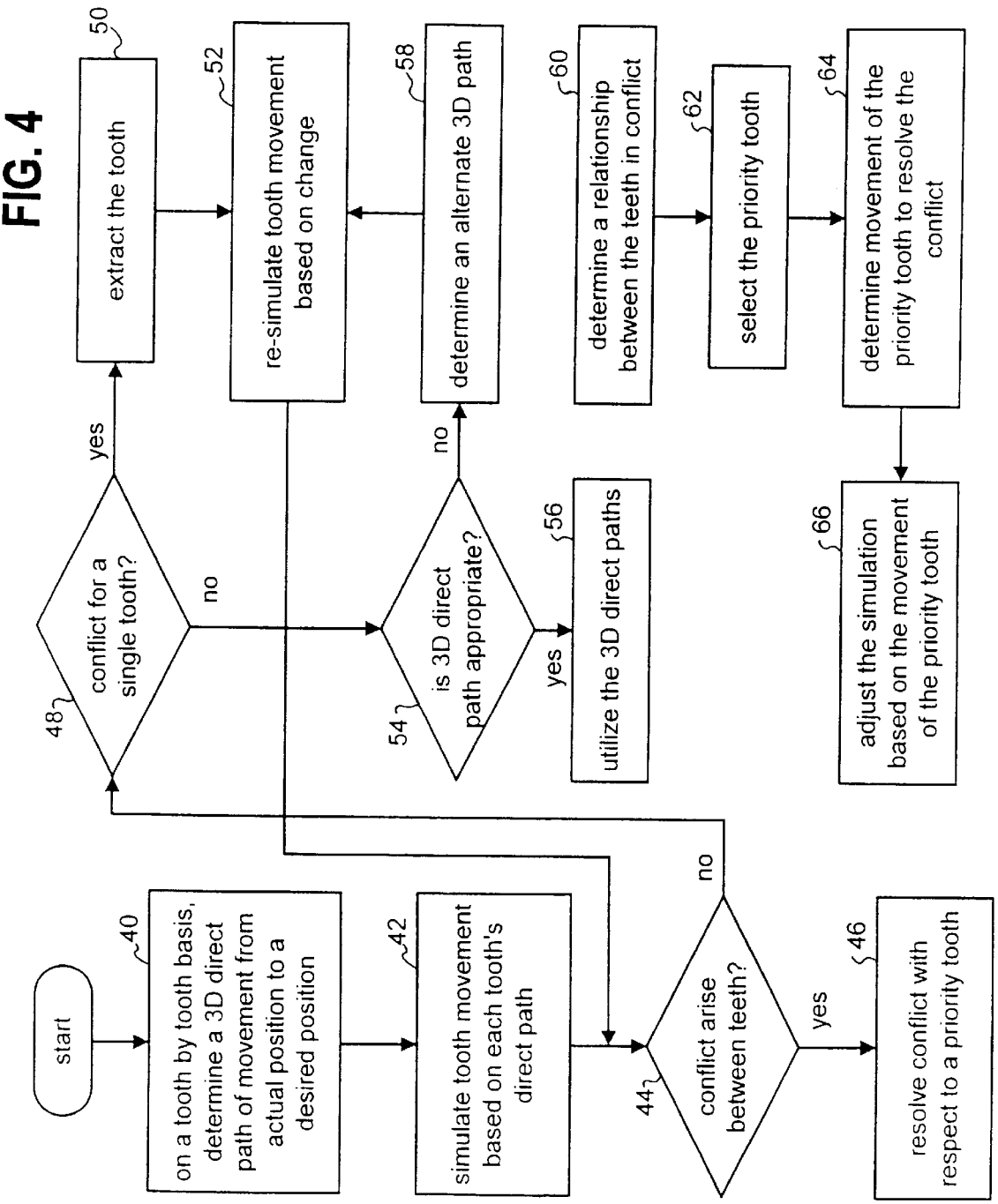

METHOD AND APPARATUS FOR SIMULATING TOOTH MOVEMENT FOR AN ORTHODONTIC PATIENT

TECHNICAL FIELD OF THE INVENTION

This invention relates generally to the practice of orthodontics and in particular to a method and apparatus for treating an orthodontic patient.

BACKGROUND OF THE INVENTION

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Unfortunately, the current innovations to change the practice of orthodontic from an art to a science have only made limited progress. This limit is due to, but not restricted to, the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of millimeter or less and an angle of a few degrees or less) can cause a different force system (i.e., magnitude of movement and direction of movement) than the desired force system to be applied to the tooth. As such, the tooth will not be repositioned to the desired location.

Another issue with the brackets being the focal point is that once the brackets are placed on the teeth, they are generally fixed for the entire treatment. As such, if the treatment is not progressing as originally calculated, the orthodontist uses his or her expertise to make the appropriate changes. The treatment may not progress as originally calculated for several reasons. For example, misplacement of a bracket, misapplication of a bend in the wire, loss or attrition of a bracket, bonding failure, the patient falls outside of the "normal" patient model (e.g., poor growth, anatomical constraints, etc.), patient lack of cooperation in use of auxiliary appliance, etc. are factors in delayed treatment results. When one of these conditions arise, the orthodontist utilizes his or her expertise to apply manual bends to the wire to "correct" the errors in treatment. Thus, after the original scientific design of the brackets, the practice of the orthodontic converts back to an art for many patients for the remainder of the treatment.

Another issue with the brackets being the focal point is that customized brackets are expensive. A customized bracket is produced by milling a piece of metal (e.g., stainless steel, aluminum, ceramic, titanium, etc.) and tumble polishing the milled bracket. While the milling process is very accurate, some of the accuracy is lost by tumble polishing. Further accuracy is lost in that the placement of the brackets on the teeth and installation of the wire are imprecise operations. As is known, a slight misplacement of one bracket changes the force on multiple teeth and hinders treatment. To assist in the placement of the custom brackets, they are usually shipped to the orthodontist in an installation jig. Such an installation jig is also expensive. Thus, such scientific orthodontic treatment is expensive and has many inherent inaccuracies.

Therefore, a need exists for a method and apparatus that simulates tooth movement thereby enabling a scientific approach to orthodontics throughout the treatment, maintains treatment costs, and provides a more consistent treatment time.

BRIEF DESCRIPTION OF THE DRAWINGS

FIGS. 3A–3C illustrate a graphical representation of tooth movement in three-dimensional space from an actual tooth position to a desired tooth position in accordance with the present invention; and FIG. 4 illustrates a logic diagram of a method for simulating tooth movement for an orthodontic patient in accordance with the present invention.

DETAILED DESCRIPTION OF A PREFERRED EMBODIMENT

Generally, the present invention provides a method and apparatus for simulating tooth movement for an orthodontic patient. Such a method and apparatus include processing that begins by determining, on a tooth by tooth basis, a three-dimensional direct path of movement from a three-dimensional digital model of an actual orthodontic structure and a three-dimensional digital model of a desired orthodontic structure. The processing continues by simulating tooth movement for a plurality of teeth based on each tooth's corresponding three-dimensional direct path. The process then determines whether a conflict arises between at least two teeth of the plurality of teeth, or for a single tooth, during the simulating. If a conflict arose between at least two teeth, the conflict is resolved with respect to a priority tooth of the teeth in conflict. With such a method and apparatus, automation of orthodontic care can be realized thus changing orthodontic care from an art to a science.

Figure 1A:
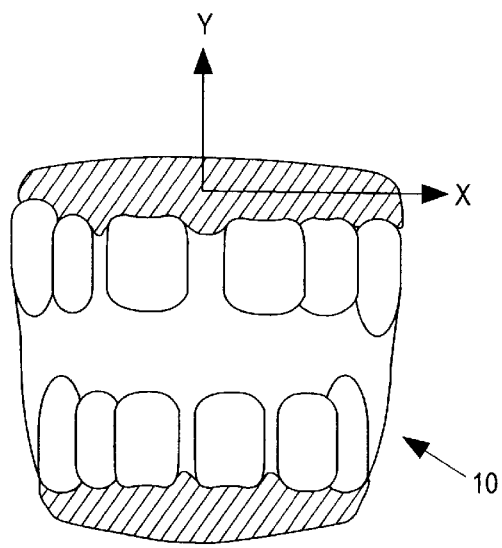
FIGS. 1A–1E illustrate several different views of a three-dimensional digital model of an actual orthodontic structure in accordance with the present invention.
Figure 1B:
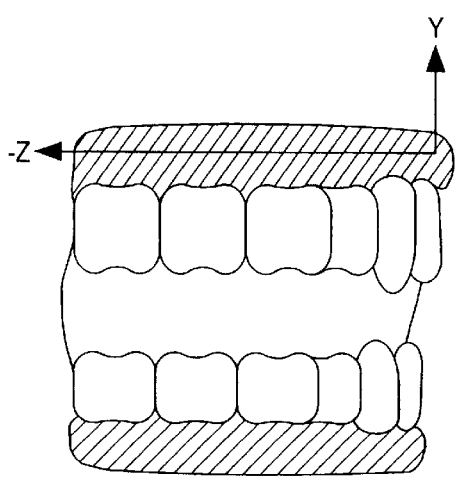
Figure 1C:
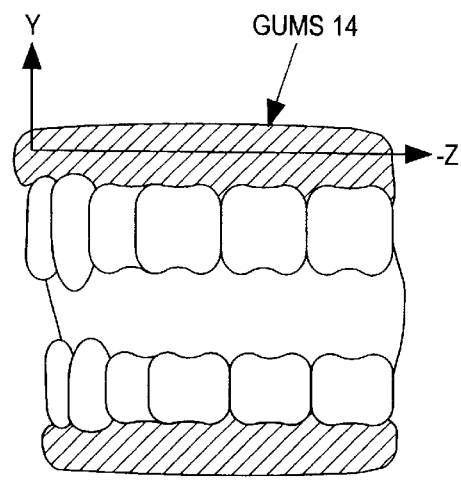
Figure 1D:
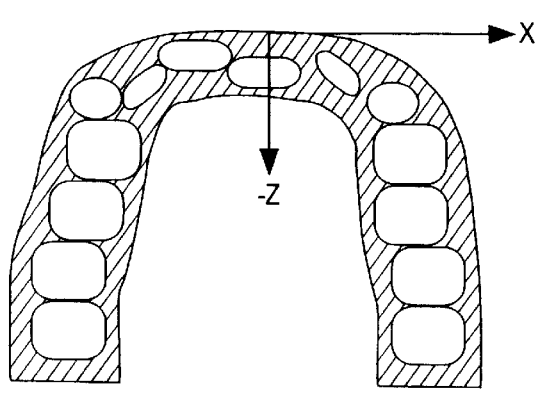
Figure 1E:
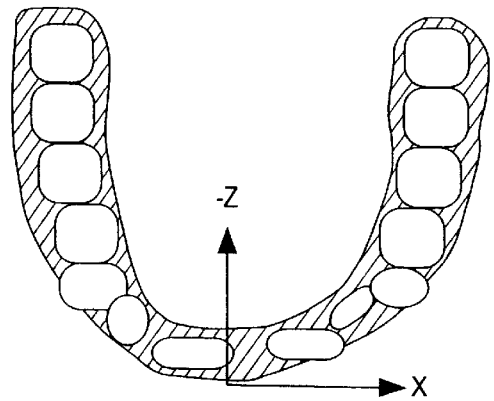
Figure 2A:
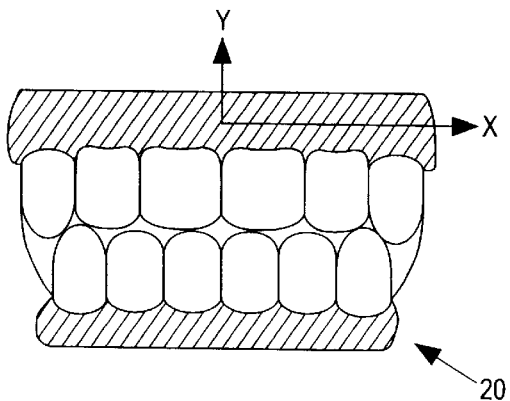
FIGS. 2A–2E illustrate several different views of a three-dimensional digital model of a desired orthodontic structure in accordance with the present invention.
Figure 2B:
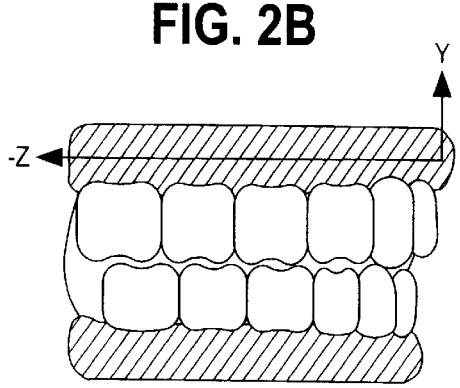
Figure 2C:
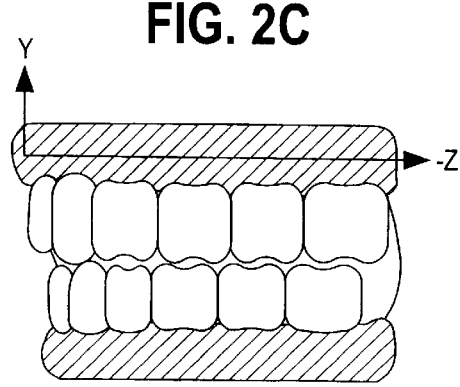
Figure 2D:
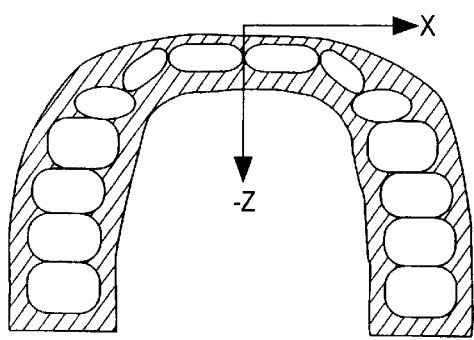
Figure 2E:
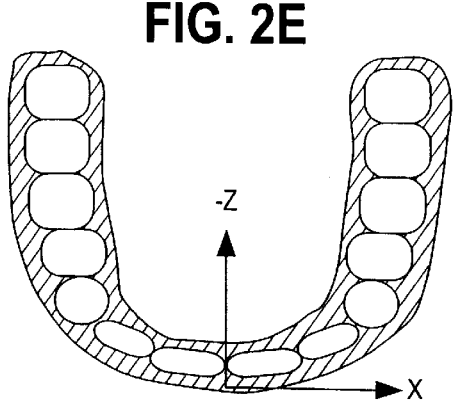

The present invention can be more fully described with reference to FIGS. 1 through 4. FIGS. 1A–1E illustrate several different views of a graphical diagram of a three-dimensional digital model of an actual orthodontic structure 10 that includes a plurality of teeth 12 and gums 14. The three-dimensional model 10 is mapped to x, y, z space. For a detailed discussion of the generation of the three-dimensional digital model of an actual orthodontic structure 10 refer to a co-pending patent application having Ser. No. 09/452,034 entitled METHOD AND APPARATUS FOR PRODUCING A THREE-DIMENSIONAL DIGITAL MODEL OF AN ORTHODONTIC PATENT, having a filing date the same as the present patent application and is assigned to the same assignee as the present patent application.

FIGS. 2A–2E illustrate several different views of a three-dimensional digital model of a desired orthodontic structure 20. The desired orthodontic structure 20 is mapped to three-dimensional space and has the teeth positioned in the ideal, or desired spot. The generation of the three-dimensional digital model of the desired orthodontic structure 20 is described in greater detail in co-pending patent application having Ser. No. 09/452,031 entitled METHOD AND APPARATUS FOR GENERATING A DESIRED THREE-DIMENSIONAL DIGITAL MODEL OF AN ORTHODONTIC STRUCTURE, having a filing date the same as the present patent application and being assigned to the same assignee as the present patent application.

FIGS. 3A–3C illustrate a graphical representation of a tooth and its corresponding three-dimensional direct path of movement. As shown, in a front, side and bottom view, the actual tooth position 30 is referenced by a three-dimensional axis system that is mapped to the center of the tooth. As one of average skill in the art will appreciate, the three-dimensional axis system for the tooth may map to any particular physical point on the tooth or exterior to the tooth.

In each of the front, side and bottom views, the desired tooth position 32 is shown. Accordingly, for the tooth to move from the actual tooth position 30 to the desired tooth position 32, it must traverse three planes of space. As shown in the front view, the tooth movement is along a second plane and has a second plane rotation angle 36. In the side view, the tooth moves in a first plane in accordance with a first plane rotation angle 34. Similarly, in the bottom view, the tooth must rotate in a third plane in accordance with the third plane rotation angle 38.

The first, second and third plane rotational angles 34 through 38 are readily determined based on the geometric relationship between the actual tooth position and the desired tooth position 32. Based on these angles of rotation, a vector may be generated to reposition the tooth from its actual position 30 to the desired position 32. The three-dimensional direct path is calculated for each tooth in the upper and lower arches.

FIG. 4 illustrates a logic diagram of a method for simulating tooth movement for an orthodontic patient. The steps shown in FIG. 4 may be implemented as operational instructions, stored in memory, and executed by a processing module. Such memory and processing module may be found in an orthodontic server as discussed in co-pending application having an attorney Ser. No. 09/451,560, entitled METHOD AND APPARATUS FOR TREATING AN ORTHODONTIC PATIENT, having a filing date the same as the present patent application, and is assigned to the same assignee as the present patent application.

The process begins at step 40 where, on a tooth by tooth basis, a three-dimensional direct path of movement is determined. The three-dimensional direct path is determined from an actual tooth position in relation to a desired tooth position. Such was discussed with reference to FIG. 3. The process then proceeds to step 42 where the tooth movement for a plurality of teeth in the upper arch and lower arch is simulated based on each tooth's direct path. The simulation of the tooth movement will be based on several factors including the number of steps in the treatment, a growth factor if applicable, normalized movement of teeth for a normalized patient, uniformity of force upon each tooth for displacement, and user inputs, such as function, aesthetics, and stability. The normalized patient information will be generated from a database of orthodontic parameters that include gun density, bone density, tooth size, age, race, sex and/or any other biological and/or mechanical feature that affects tooth movement. Note that the mechanical features correspond to the types of brackets used, the type and size of arch wire used, and other orthodontic appliances used.

The process then proceeds to step 44 where a determination is made as to whether a conflict in movement arose between at least two teeth during the simulation. A conflict may arise in that the movement of one tooth interferes with the direct path movement of another tooth causing a particular tooth to not be able to obtain its desired position.

If a conflict arose between two or more teeth, the process proceeds to step 46. At step 46, the conflict is resolved with respect to a priority tooth. The resolution of the conflict is further described with reference to steps 60 through 66. At step 60, a relationship is determined between the teeth and conflict. The process then proceeds to step 62 where a priority tooth is selected between the teeth and conflict. The priority may be established based on whether the tooth is a foundation tooth, whether the conflict results from an inter-arch conflict or an intra-arch conflict, and/or whether the teeth in conflict effect other teeth in movement. For an intra-arch conflict, the actual position of the tooth will dictate whether the upper tooth is priority or the lower tooth is priority. If the lower tooth protrudes preventing the upper tooth from moving back, the lower tooth must be moved before the upper tooth can be positioned. Conversely, if the upper tooth is interfering with the lower tooth from being moved out, the upper tooth must first be moved.

The resolution of the conflict then proceeds to step 64 where movement of the priority tooth is determined to resolve the conflict. As such, the priority tooth is moved sufficiently to resolve the conflict. The process then proceeds to step 66 where the simulation is adjusted based on the movement of the priority tooth. Note that depending on the priority tooth and the conditions giving rise to the conflict, the movement of the priority tooth may be done independently of other tooth movement or in parallel with other tooth movement.

Returning to the main flow of FIG. 4, if a conflict did not arise between two or more teeth, the process proceeds to step 48. At step 48 a determination is made as to whether a conflict exists for a single tooth. Such a conflict arises when the tooth cannot obtain its desired position due to distance of movement and treatment constraints, which include, but are not limited to, number of treatments, orthodontic apparatus used, patient cooperation, and biological conditions. If so, the process proceeds to step 50 where the tooth is extracted. The process then proceeds to step 52 where the tooth movement is resimulated based on the extraction of the tooth. Note that the extraction of tooth at step 50 is done based on the digital model to test the appropriateness for extracting the tooth.

If a conflict does not arise for a single tooth, the process proceeds to step 54 where a determination is made as to whether the direct three-dimensional path is appropriate. If so, the process proceeds to step 56 where the three-dimensional direct paths are used. If the three-dimensional direct path is not appropriate for a given tooth, the process proceeds to step 58. The direct path may not be appropriate for a particular tooth based on the type of bone that the direct path lies. For example, if the direct path lies in the cortical bone, which is quite dense, the direct path may be re-routed to an indirect path that goes through softer bone such as the cancellous bone. At step 58, an alternate three-dimensional path is determined. The process then repeats at step 52 where simulation of tooth movement is again performed based on the alternate three-dimensional path.

The preceding discussion has presented a method and apparatus for simulating tooth movement for an orthodontic patient. By utilizing digital models of the actual orthodontic structure and desired orthodontic structure, an orthodontic care giver may simulate the orthodontic treatment as well as monitor the orthodontic treatment throughout the treatment process. As such, the present invention assists in the conversion of the practice of the orthodontics from an art to a science. As one of average skill in the art would readily appreciate, other embodiments may be derived from the teachings of the present invention without deviating from the scope of the claims.

What is claimed is:

1. A method for simulating tooth movement for an orthodontic patient, the method comprising the steps of:

a) determining, on a tooth by tooth basis, a three-dimensional direct path of movement from a full three-dimensional digital model of an actual orthodontic structure and a full three-dimensional digital model of a desired orthodontic structure;

b) simulating tooth movement for a plurality of teeth based on each tooth's corresponding three-dimensional direct path;

c) determining whether a conflict arises between at least two of the plurality of teeth during the simulating; and d) when the conflict arose between at least two of the plurality of teeth during the simulating, resolving the conflict with respect to a priority tooth of the at least two of the plurality of teeth.

2. The method of claim 1 further comprising:

determining an alternate three dimensional path when the three dimensional direct path is not appropriate for a given tooth but no conflict arose between at least two of the plurality of teeth during the simulating; and re-simulating the tooth movement for the plurality of teeth based on each tooth's corresponding three-dimensional direct path and the alternate three-dimensional path for the given tooth.

3. The method of claim 2 further comprising:

when the three-dimensional direct path is appropriate for each of the plurality of teeth, utilizing the three-dimensional direct paths.

4. The method of claim 1, wherein step (c) further comprises determining the conflict to arise for a single tooth when the single tooth cannot obtain the desired orthodontic structure with respect to the single tooth within constraints of treatment.

5. The method of claim 4, further comprising at least one of:

simulating extraction of the single tooth; and modifying the desired orthodontic structure with respect to the single tooth.

6. The method of claim 1, wherein step (b) further comprises simulating the tooth movement based on corresponding orthodontic parameters, wherein the corresponding orthodontic parameters includes at least one of: patient's age, patient's race, patient's sex, normalized tooth displacement vectors, growth factor, and normalized tooth size.

7. The method of claim 1, wherein step (d) further comprises:

determining a relationship between the at least two of the plurality of teeth in the conflict;

selecting the priority tooth based on at least one of: the priority tooth being a foundation tooth, inter-arch conflict, and intra-arch conflict;

determining movement of the priority tooth to resolve the conflict; and adjusting the simulating the tooth movement based on the movement of the priority tooth to resolve the conflict.

8. The method of claim 7 further comprising:
determining whether the movement of the priority tooth to resolve the conflict is an independent movement or a parallel movement.

9. An apparatus for simulating tooth movement for an orthodontic patient, the apparatus comprising:
a processing module; and
memory operably coupled to the processing module, wherein the memory stores data representing a full three-dimensional digital model of an actual orthodontic structure and data representing a full three-dimensional digital model of a desired orthodontic structure and wherein the memory further includes operational instructions that cause the processing module to: (a) determine, on a tooth by tooth basis, a three-dimensional direct path of movement from said three dimensional digital model of an actual orthodontic structure and said three dimensional digital model of a desired orthodontic structure; (b) simulate tooth movement for a plurality of teeth based on each tooth's corresponding three-dimensional direct path; and (c) determine whether a conflict arises between at least two of the plurality of teeth during the simulating.

10. The apparatus of claim 9, wherein the memory further comprises operational instructions that cause the processing module to:
determine an alternate three dimensional path when the three dimensional direct path is not appropriate for a given tooth but no conflict arose between at least two of the plurality of teeth during the simulating; and
re-simulate the tooth movement for the plurality of teeth based on each tooth's corresponding three-dimensional direct path and the alternate three-dimensional path for the given tooth.

11. The apparatus of claim 9, wherein the memory further comprises operational instructions that cause the processing module to:
simulate the extraction of the single tooth; and
modify the desired orthodontic structure with respect to the single tooth.

12. The apparatus of claim 9, wherein the memory further comprises operational instructions that cause the processing module to: simulate the tooth movement based on corresponding orthodontic parameters, wherein the corresponding orthodontic parameters includes at least one of: patient's age, patient's race, patient's sex, normalized tooth displacement vectors, growth factor, and normalized tooth size.

13. The apparatus of claim 9, wherein the memory further comprises operational instructions that cause the processing module to:
determine movement of a selected priority tooth to resolve the conflict; and
adjust the simulating of the tooth movement based on the movement of the priority tooth to resolve the conflict.

14. The apparatus of claim 13, wherein the memory further comprises operational instructions that cause the processing module to:
determine whether the movement of the priority tooth to resolve the conflict is an independent movement or a parallel movement.

15. A method for simulating tooth movement for an orthodontic patient, the method comprises the steps of:
a) determining, on a tooth by tooth basis, a three-dimensional direct path of movement from a full three-dimensional digital model of an actual orthodontic structure and a full three-dimensional digital model of a desired orthodontic structure;
b) simulating tooth movement for a plurality of teeth based on each tooth's corresponding three-dimensional direct path;
c) determining whether a conflict arises with an adjacent structure in the mouth in the tooth movement for at least one tooth of the plurality of teeth; and
d) when the conflict arises during the simulating, resolving the conflict for the at least one tooth.

16. The method of claim 15 further comprising at least one of:
simulating the extraction of the at least one tooth; and
modify the desired orthodontic structure with respect to the at least one tooth.

17. The method of claim 15, further comprising:
determining an alternate three dimensional path when the three dimensional direct path is not appropriate for a given tooth but no conflict arose during the simulating; and
re-simulating the tooth movement for the plurality of teeth based on each tooth's corresponding three-dimensional direct path and the alternate three-dimensional path for the given tooth.

18. An apparatus for simulating tooth movement for an orthodontic patient, the apparatus comprising:
a processing module; and
memory operably coupled to the processing module, wherein the memory stores data representing a full three-dimensional digital model of an actual orthodontic structure and data representing a full three-dimensional digital model of a desired orthodontic structure and wherein the memory further includes operational instructions that cause the processing module to: (a) determine, on a tooth by tooth basis, a three-dimensional direct path of movement from said three-dimensional digital model of an actual orthodontic structure and said three-dimensional digital model of a desired orthodontic structure; (b) simulate tooth movement for a plurality of teeth based on each tooth's corresponding three-dimensional direct path; and (c) determine whether a conflict arises in the tooth movement for at least one tooth of the plurality of teeth.

19. The apparatus of claim 18, wherein the memory further comprises operational instructions that cause the processing module to:
determine an alternate three dimensional path when the three dimensional direct path is not appropriate for a given tooth but no conflict arose during the simulating; and
re-simulate the tooth movement for the plurality of teeth based on each tooth's corresponding three-dimensional direct path and the alternate three-dimensional path for the given tooth.

20. The apparatus of claim 18, wherein the memory further comprises operational instructions that cause the processing module to:
simulate the extraction of the at least one tooth; and
modify the desired orthodontic structure with respect to the at least one tooth.

* * * * *